US011858890B2

(12) United States Patent
Krill et al.

(10) Patent No.: US 11,858,890 B2
(45) Date of Patent: *Jan. 2, 2024

(54) REACTOR AND PROCESS FOR PRODUCING ALKYL (METH)ACRYLATES (71) Applicant: Röhm GmbH, Darmstadt (DE)

(72) Inventors: Steffen Krill, Muehltal (DE); Belaid Ait Aissa, Darmstadt (DE); Andreas Rühling, Darmstadt (DE); Mounir Stitou, Wuppertal (DE); Andreas Gräff, Riedstadt-Erfelden (DE); Olaf Merker, Gondelsheim (DE)

(73) Assignee: Röhm GmbH, Darmstadt (DE)

( * ) Notice: Subject to any disclaimer, the term of this patent is extended or adjusted under 35 U.S.C. 154(b) by 51 days.

This patent is subject to a terminal disclaimer.

(21) Appl. No.: 17/804,057

(22) Filed: May 25, 2022

(65) Prior Publication Data

US 2022/0388941 A1 Dec. 8, 2022

(30) Foreign Application Priority Data

May 28, 2021 (EP) .................................... 21176498

(51) Int. Cl.
C07C 67/42 (2006.01)
B01J 19/18 (2006.01)
B01J 35/02 (2006.01)

(52) U.S. Cl.
CPC ........... C07C 67/42 (2013.01); B01J 19/1856 (2013.01); B01J 35/023 (2013.01); B01J 35/026 (2013.01); B01J 2219/00481 (2013.01)

(58) Field of Classification Search
CPC ....... C07C 67/42; C07C 51/235; C07C 67/08; C07C 69/653; C07C 57/04; C07C 67/39;

(Continued)

(56) References Cited

U.S. PATENT DOCUMENTS 5,288,673 A   2/1994 Behrmann et al.
5,417,930 A   5/1995 McDonald, Jr. et al.
(Continued)

FOREIGN PATENT DOCUMENTS

CN  101314120  12/2008
CN  104418309   3/2015
(Continued)

OTHER PUBLICATIONS

Acrivos et al. "Enhanced sedimentation in settling tanks with inclined walls", Journal Fluid. Mech., vol. 92, Part 3, 1979, pp. 435-457.

(Continued)

Primary Examiner — Jafar F Parsa
(74) Attorney, Agent, or Firm — Grüneberg and Myers PLLC (57) ABSTRACT A novel process can be used for a heterogeneously catalysed oxidation reaction, in the presence of a pulverulent noble metal-containing catalyst, where (meth)acrolein, an alkyl alcohol, in particular methanol, and an oxygen-containing gas are converted to an alkyl (meth)acrylate, in particular methyl (meth)acrylate. A corresponding reactor suitable for performing the reaction is also useful. The process allows for an effective retention of the particulate catalyst and the continuous discharge of fines fractions of the catalyst powder which are present, particularly in a fresh catalyst batch as a consequence of its preparation. Such fines fractions may also be produced by abrasion during the reaction. The process allows for effective recycling, recovery, and utilization of these discharged catalyst fractions.

20 Claims, 4 Drawing Sheets

(58) Field of Classification Search
CPC ..... C07C 69/54; B01J 19/1856; B01J 35/023; B01J 35/026

See application file for complete search history.

(56) References Cited

U.S. PATENT DOCUMENTS

| | | |
|---|---|---|
| 8,450,235 B2 | 5/2013 | Suzuki et al. |
| 9,617,199 B2 | 4/2017 | Krill et al. |
| 9,963,417 B2 | 5/2018 | Krill et al. |
| 10,596,539 B2 | 3/2020 | Lygin et al. |
| 11,124,471 B2 | 9/2021 | Lygin et al. |
| 11,279,667 B2 | 3/2022 | Krill et al. |
| 11,299,449 B2 | 4/2022 | Krill et al. |
| 2016/0251301 A1 | 9/2016 | Krill et al. |
| 2016/0280628 A1 | 9/2016 | Krill et al. |
| 2019/0099731 A1 | 4/2019 | Lygin et al. |
| 2021/0032386 A1 | 2/2021 | Krill et al. |
| 2021/0047259 A1 | 2/2021 | Lygin et al. |
| 2021/0269385 A1 | 9/2021 | Krill et al. |
| 2022/0204436 A1 | 6/2022 | Krill et al. |

FOREIGN PATENT DOCUMENTS

| | | |
|---|---|---|
| EP | 3 235 560 | 10/2017 |
| EP | 3 456 704 | 3/2019 |
| JP | H09-248403 | 9/1997 |
| JP | H10-94705 | 4/1998 |
| WO | 2012/152600 | 11/2012 |

OTHER PUBLICATIONS

Suzuki et al., "Aerobic Oxidative Esterification of Aldehydes with Alcohols by Gold-Nickel Oxide Nanoparticle Catalysts with a Core-Shell Structure", American Chemical Society—Catalysis, vol. 3, 2013, pp. 1845-1849.

U.S. Pat. No. 9,617,199, Apr. 11, 2017, 2016/0251301, Krill et al.
U.S. Pat. No. 9,963,417, May 8, 2018, 2016/0280628, Krill et al.
U.S. Pat. No. 10,596,539, Mar. 24, 2020, 2019/0099731, Lygin et al.
U.S. Pat. No. 11,124,471, Sep. 21, 2021, 2021/0047259, Lygin et al.
U.S. Appl. No. 16/637,575, filed Feb. 7, 2020, 2021/0032386, Krill et al.
U.S. Pat. No. 11,299,449, Apr. 12, 2022, 2021/0269385, Krill et al.
U.S. Appl. No. 17/597,345, filed Jan. 4, 2022, 2022/0204436, Krill et al.
U.S. Appl. No. 17/753,245, filed Feb. 24, 2022, Krill et al.
U.S. Appl. No. 17/664,924, filed May 25, 2022, Krill et al.

REACTOR AND PROCESS FOR PRODUCING ALKYL (METH)ACRYLATES

CROSS-REFERENCE TO RELATED APPLICATIONS

This application claims priority to European Application No. 21176498.0, filed on May 28, 2021, the content of which is hereby incorporated by reference in its entirety.

BACKGROUND OF THE INVENTION

Field of the Invention

The present invention relates to a novel process and reactors suitable therefor for performing a heterogeneously catalysed oxidation reaction of (meth)acrolein, alkyl alcohol and an oxygen-containing gas to afford alkyl (meth)acrylate in the presence of a pulverulent noble metal catalyst. A particular aspect here is the effective retention of the particulate catalyst and the continuous discharge of fines fractions of the catalyst powder which are present in the fresh catalyst as a consequence of its preparation or are produced by abrasion during the reaction. A further feature is the effective recycling, recovery and utilization of these discharged amounts of catalyst.

The term (meth)acrylates is hereinbelow to be understood as meaning derivatives of acrylic acid and of methacrylic acid.

There are plentiful descriptions in the technical literature of heterogeneously catalysed reactions in a liquid phase. These include, for example, the cobalt-catalysed Fischer-Tropsch synthesis, palladium- and nickel-catalysed hydrogenations with hydrogen, and numerous oxidation reactions.

Against this background, the reactor system according to the present invention has made it possible to achieve prolonged problem-free continuous operation of such processes with activities and selectivities remaining unchanged, wherein the catalyst used may be employed for longer and noble metal-containing discharges from the reactor may be recovered and recycled.

This gives rise to the possibility of performing such processes in a manner that is as simple as possible, economically viable and environmentally benign.

Description of Related Art

Heterogeneously catalysed processes in which at least one liquid phase is present in addition to the solid phase are often performed in so-called slurry reactors.

These processes have substantial differences and also fundamental advantages compared to the widely used fixed-bed gas-phase processes (for example production of acrylonitrile from propene/ammonia/air or gas-phase production of (meth)acrolein and (meth)acrylic acid from corresponding precursors) in which the catalyst is fixed in the reactor as a pellet or shaped body. Slurry reactors using suspended catalyst particles/powders find use especially where gas-phase fixed-bed catalysis does not show adequate selectivities and yields, especially as a result of the high reaction temperatures required.

This generally applies inter alia to a number of strongly exothermic reactions from the group of partial oxidation of organic substrates. This especially applies to the oxidation of (meth)acrolein to (meth)acrylic acid, which may in a second step be esterified with methanol to MMA.

Methyl methacrylate (MMA) is a monomer and starting material for the production of polymethyl methacrylate (PMMA), coatings, resins and basis for a multiplicity of other chemical products and applications. There are various competing processes for the production of (meth)acrylates and methacrylic acid as basic monomers of the chemical industry. These proceed from various raw materials and intermediates, for instance from acetone cyanohydrin (ACH)—formed by reaction of acetone with hydrocyanic acid—ethylene, propylene or isobutene. The global production landscape continues to be dominated by C3-based MMA processes starting from acetone as the raw material. C4-based processes have become established especially in Asia. Important new developments of MMA production processes are found in the field of C2-based processes with ethylene as the starting material, primarily the ALPHA process of Mitsubishi Chemical Corp. (MCC) and the new LIMA process of Evonik.

The general prior art is described substantially in current reviews and overview articles.

a.) Nexant, CHEMSYSTEMS PERP PROGRAM, Methyl Methacrylate PERP 08/09-7 Mar. 2010,
b.) R. J. Chang, S. Naqvi, IHS Chemical PEP Report Methyl Methacrylate (MMA) Process Summary 2014 May.
c.) "Trends and Future of Monomer-MMA Technologies", K. Nagai & T. Ui, Sumitomo Chemical Co., Ltd.; Basic Chemicals Research Laboratory, www.sumitomochem.co.jp/english/rd/report/theses/docs/20040200_30a.pdf, 2005.
d.) "Viele Wege führen zum Methacrylsäuremethylester" [Many routes lead to methyl methacrylate], S. Krill, A. Ruehling, H. Offermans, Chem. Unserer Zeit, 2019, 53; © 2019 Wiley-VCH Verlag GmbH & Co. KGaA, Weinheim A process based on isobutene or MTBE or tert-butanol is also described in detail here. In this overall two-stage process, the (meth)acrolein obtained by gas-phase oxidation over a fixed-bed catalyst is condensed, purified and in the second stage reacted with methanol in the liquid phase by direct oxidative esterification (DOE) to MMA.

A characteristic feature of this process is the use of a heterogeneous, supported Pd—Pb-based catalyst which especially features excellent longevity of use and very high MMA selectivities of up to 93%. The pulverulent catalyst is employed in a slurry reactor, i.e. in a triphasic reaction system consisting of liquid reaction matrix, the suspended catalyst and the oxygen-containing gas, in the simplest case air. As advantageous as the high selectivities of the DOE process make it appear there was nevertheless a considerable need for development since the catalyst has a propensity for lead losses, so-called leaching, which cause considerable cost and inconvenience during workup. A soluble lead compound must be metered into the reactor to maintain catalyst activity.

Meanwhile, a second generation of catalysts has been developed which are based on a core-shell catalyst consisting of NiOx and gold and solve key disadvantages and problems of the original process. In contrast to the first generation of catalysts, long-term stability was significantly increased by a number of years. These new developments are described in S. Stahl and P. Alsters, "Liquid Phase Aerobic Oxidation Catalysis", publ. 17 Aug. 2016, Print ISBN 9783527337811, Wiley-VCH Verlag GmbH, see Ken Suzuki, pages 209-2018 and in U.S. Pat. No. 8,450,235.

A known variant of such reactors is that of reactors having an inner tube known as a "draft tube", which allow internal circulation. For instance, U.S. Pat. No. 5,288,673 describes the use of a slurry reactor with a draft tube for a Fischer-Tropsch synthesis for production of hydrocarbons from synthesis gas.

CN 104418309 describes a slurry reactor with a draft tube for hydrogen peroxide production in a heterogeneously catalysed hydrogenation reaction of anthraquinone. The catalyst concentration used is about 10 g/l (<0.01 kg/kg of mixture) and is thus relatively low. The direction of flow in the draft tube from the bottom upwards constantly conveys a high proportion of the catalyst back into the tube.

WO 2012/152600 describes an ammoxidation of cyclohexanone which is performed with a heterogeneous TS-1 catalyst as a triphasic (gaseous-solid-liquid) reaction. Both the heat transfer and the mass transfer in this process can be distinctly improved when a cylindrical draft tube is used. The reactants are metered in here at different points. One metered addition takes place below the draft tube (in this case $NH_3$), one from above it (in this case $H_2O$) and optionally one from the side (in this case cyclohexanone, for example). Filtration is effected with the aid of many candle filters having a high total area. These are positioned at the midpoint of the reactor height and at the outer edge of the draft tube. According to the description, the process can be performed for 1 year without interruption and filter backwashing. After one year, the filters then have to be cleaned.

The use of slurry reactors with internal circulation for reactions in which formation of deposits is possible, especially for reactions where polymerizable substances are produced for example, is not described. U.S. Pat. No. 5,417,930 even suggests that a slurry-type reactor with internal circulation via one or more draft tubes can be particularly beneficial for the polymerization of polymerizable substances. For reactions including such substances, the prior art discloses a number of reactors for performing a heterogeneously catalysed reaction with external circulation of the slurry mixture. Thus for example U.S. Pat. No. 5,969,178 describes a process for continuous production of MMA from isobutene or tert-butanol via methacrolein. An oxidative esterification of readily polymerizable methacrolein is carried out as the last step of the process in a bubble column with external circulation. In this respect, the reactor is described as an "external circulation type bubble column reactor".

CN 101314120 describes a loop slurry reactor with external circulation of the slurry mixture for performance, for example, of the Fischer-Tropsch process. All reactors having external circulation of the slurry mixture require quite complex reactor designs and slurry conveying apparatuses that have to be safeguarded, for example, by means of further pumps. Therefore, and for other reasons, these systems thus have disadvantages compared to systems having internal circulation. In summary, the following aspects of the process according to the prior art are in need of improvement and desirable:

- simplest possible construction of reactor and thus no restriction on suitability for scale-up
- the use of substances that settle out or are readily polymerizable is possible
- use of high catalyst concentrations and hence higher throughput
- reduced abrasion of the heterogeneous catalyst used
- good commixing of the reactor phases
- long catalyst on-stream time, robust operation without interruption, very short maintenance phases if any
- the possibility of installation of simplified filtration systems for continuous separation of the heterogeneous catalyst from the slurry mixture without shutdown times.

The novel LiMA process for producing MMA combines the highly efficient process stages of C2-based methacrolein synthesis starting from ethylene and synthesis gas to afford methacrolein with the highly efficient direct oxidative esterification of methacrolein to MMA. Precisely this combination of established steps with novel developments has made it possible to provide a novel, highly efficient process for MMA production. In the first stage, this process reacts ethylene with synthesis gas to afford propionaldehyde, wherein known rhodium-based phosphine or phosphite ligands are advantageously used as catalysts. In a modified process, reaction with formalin affords almost quantitative yields of methacrolein as an intermediate. In the last step, methacrolein is then converted directly into MMA in the presence of methanol over a noble metal-based heterogeneous catalyst, thus achieving high conversions and virtually quantitative selectivities.

In Angew, Chem. 2016, 128, 14420-14428, T 2016 Wiley-VCH Verlag GmbH & Co. KGaA, Weinheim, R. Cirminna and M. Pagliaro describe the essential aspects and features of a nanoparticulate gold-$NiO_x$-based catalyst of the Japanese MMA manufacturer Asahi Kasai Chemicals.

What appears to be essential to the performance of the active gold catalyst is inter alia the use of a mixed-metal-oxide support material which consists of alumina, silica and magnesium oxide and allows preparation of the complex gold-$NiO_x$ system. K. Suzuki, H. Ishida et al, describe the production of catalysts $AuNiO_x/SiO_2$—$Al_2O_3$—MgO and a reaction system in ACS Catal. 2013, 3, 1845-1849, wherein the reaction of methacrolein in an oxidative esterification with methanol and an oxygen-containing gas, such as air in the simplest case, is performed continuously in a laboratory apparatus. These studies are pivotal to catalyst selectivity for the reaction, but give no indication of how an industrial-scale reactor may be configured to efficiently retain the catalyst and thus maintain performance in long-term operation.

A reactor for performing the oxidative esterification of methacrolein to MMA for example is described in EP 3 235 560. This document describes for example circulation of the triphasic medium through a draft tube, i.e. a zone in which medium is conveyed downwards by means of a stirrer, while the gasified reaction space has the opposite flow. This is done to produce catalyst concentration gradients. There is a high catalyst concentration in the lower portion of the reactor and a lower catalyst concentration in the upper portion. Separation systems for achieving continuous more or less catalyst-free removal of product medium from the reactor are also proposed. This is accomplished with filters which are particularly preferably to have a retention of 10 to 50 μm. An additional preseparation of the catalyst by an assembly of inclined elements, so-called inclined settlers, is described.

Fines fractions in the catalyst and fines fractions that may be formed by abrasion during the reaction cannot be effectively retained/recovered according to this method. Another problem with this system is that gas separation before the filtration system is not described. However, both in the operation of the filter and in the inclined settling, gas fractions result in partial or complete failure of the separation effect and also lead to polymeric deposits of monomers in the reaction matrix.

Since the reactor is preferably to be used for a continuous process, the heterogeneous catalyst should be able to be continuously filtered out of the reaction mixture. To this end, it is preferable to use filters present in the reactor, particularly preferably at the periphery of a zone 2 in the upper portion of the reactor. In particular, irrespective of the other chosen embodiments of the invention, preference is given to installing at least one continuously operable and backwashable filter in the upper portion of said zone 2.

Alternatively or in addition, the reaction mixture is continuously discharged from the reactor and filtered via at least one external filter. Thereafter, the catalyst is optionally subjected to further treatment after the filtration and passed partly or completely back into the reactor. This further treatment may for example be washing, reactivation or separation according to particle size.

Furthermore, according to EP 3 235 560 an additional settling system may also be installed upstream of such filters or else at the periphery of the reactor. This may be a specific zone with laminar flow, where a major part of the catalyst used undergoes sedimentation. Such sedimentation thus takes place before the actual filtration. One possible variant of such a sedimentation system is, for example, an assembly composed of inclined elements, for example tubes or inclined metal sheets. The principle of operation of such systems is further described in Journal of Fluid Mechanics/Volume 92/Issue 03/June 1979, pp 435-457 and in "Enhanced sedimentation in vessels having inclined walls" in Theory of Dispersed Multiphase Flow: Proceedings of an Advanced Seminar Conducted by the Mathematics Research Center The University of Wisconsin-Madison May 26-28, 1982. Details of use for an oxidation reaction, for example, are given in JP 10-094705 A and JP 09-248403 A.

JP 09-248403 A moreover describes an apparatus for workup of a triphasic (liquid-solid-gas) reaction mixture as may be employed for oxidative direct esterification of methacrolein to MMA. The chosen design of the inclined settler in conjunction with a degassing zone and a downcomer results in pressure differences over the vertically arranged inclined tube elements; the downcomer/inclined settler zone is degassed and thus largely depleted in oxygen, thus resulting in more reducing conditions prevailing here. One problem observed is that of short-circuit flows inside the inclined settler elements. This results in increased formation of the byproducts isobutyraldehyde and methyl isobutyrate, i.e. in undesired hydrogenation products of methacrolein and MMA itself. In this publication, these problems are solved by incorporating throttling elements into the inclined settler, i.e. internals which retard, hold up and thus even out the flow in the inclined settler elements. The problem of fine discharge of catalyst constituents and fines fractions which occur as a result of abrasion during long-term performance of the reaction is not described here and remains unaddressed.

JP 10-094705 A further describes a similar separation system for solid-liquid-gas reaction matrices based on the example of methacrolein conversion into MMA now with the additional feature of integration of the separation apparatus into a reactor tank (CSTR system). A key feature is a sidewall in the reactor which fulfils the function of the downcomer. The inclined settler elements may be arranged inside and outside the reactor shell and this document too describes throttles, diaphragms inside the inclined settler elements which even out the flow and thus reduce the problem of byproduct formation.

Characterizing features for both Japanese patent applications are the operating parameters for the downcomer and the inclined settler. Whereas in the downcomer portion a very high velocity of the degassed slurry is established (0.5 to 1.5 m/sec), the discharge velocity at the outlet of the inclined elements is 0.004 m/sec (0.4 cm/sec or 14.4 m/h). This high velocity difference of the downcomer velocity relative to the discharge velocity (0.5/0.004=factor of 125) is a consequence of the chosen design.

SUMMARY OF THE INVENTION

Problem

The problem addressed by the present invention was that of improving the process for the oxidative esterification of (meth)acrolein to alkyl (meth)acrylates in such a way that it may be operated for the longest possible on-stream times without replacement of the catalyst. This means a long catalyst on-stream time, robust operation without interruption and very short maintenance phases, if any, during ongoing operation.

A further problem addressed was especially that of ensuring that the catalyst fines fractions already present upon initial charging or formed as abraded material during operation may be efficiently separated and discharged in the course of ongoing operation.

A further problem addressed was that of nevertheless being able to perform the process with high catalyst concentrations and thus a higher throughput.

Solution

The problems are solved by a novel process for producing alkyl (meth)acrylates, preferably MMA, starting from (meth)acrolein, by the reaction thereof with an alkyl alcohol, preferably methanol, in the presence of an oxygen-containing gas and a particulate, pulverulent catalyst in the liquid phase. This novel process is characterized in that
 a. a portion of the employed catalyst powder is discharged from the reactor in a classifying manner together with the product solution during the reaction,
 b. the catalyst fraction remaining in the reactor has a narrower average particle size distribution shifted to higher particle sizes compared to the catalyst discharge,
 c. the catalyst discharge according to a. is collected in at least one further filter,
 d. the catalyst discharge is optionally at least partially recycled into the reactor and
 e. the catalyst discharge is optionally at least partially removed and sent to a workup for recovery of at least one of the employed catalyst metals.

The invention also includes the following embodiments:
1. Process for producing alkyl (meth)acrylates starting from (meth)acrolein by reaction thereof with an alkyl alcohol in the presence of an oxygen-containing gas and a particulate, pulverulent catalyst in the liquid phase, characterized in that
 a. a portion of the employed catalyst powder is discharged from the reactor in a classifying manner together with the product solution during the reaction during the reaction,
 b. the catalyst fraction remaining in the reactor has a narrower average particle size distribution shifted to higher particle sizes compared to the catalyst discharge compared to the catalyst discharge,
 c. the catalyst discharge according to a. is collected in at least one further filter, d. the catalyst discharge is optionally at least partially recycled into the reactor and
e. the catalyst discharge is optionally at least partially removed and sent to a workup for recovery of at least one of the employed catalyst metals.

2. Process according to embodiment 1, characterized in that
the oxidative conversion of methacrolein employs a pulverulent fresh catalyst which comprises gold or palladium as the central active oxidation metal in a concentration of between 0.1% by weight and 10% by weight based on the total weight including further support material, in that
the particles of the catalyst have a size of 0.1 to 300 µm, wherein more than 95% by volume of the catalyst particles present have a size of less than 200 µm, and in that more than 50% by volume of the catalyst particles have a size between 10 and 90 µm and in that
the fines fraction of the catalyst particles in the reactor having a size of 0.1 µm to 10 µm is less than 10% by volume.

3. Process according to embodiments 1 or 2, characterized in that
less than 0.5% by weight per hour of the catalyst powder present in the reactor are discharged from the reactor in a classifying manner together with the product solution during the reaction, in that in the catalyst fraction remaining in the reactor after 1000 operating hours more than 98% by volume of all catalyst particles have a particle size greater than 10 µm, in that
the catalyst discharge is collected in at least one further filter which allows retention of particles of 1 to 30 µm in size and in that
the particles retained in the filters downstream of the inclined settler are to an extent of more than 50% by volume particles smaller than 30 µm.

4. Process according to at least one of embodiments 1 to 3, characterized in that
the employed pulverulent catalyst has an average particle size distribution of 30 to 100 µm and in that
the fines fraction discharged with the reactor medium has an average particle size distribution of 1 to 15 µm.

5. Process according to at least one of embodiments 1 to 4, characterized in that the alkyl alcohol is methanol and the alkyl methacrylate is MMA.

6. Process according to at least one of embodiments 1 to 6, characterized in that a particle collective consisting to an extent of at least 50% by volume of particles smaller than 30 µm is continuously discharged from the reactor and is supplied to the filters in suspended form in a reaction medium containing MMA, methacrylic acid, water and methanol.

7. Process according to at least one of embodiments 1 to 6, characterized in that the reaction medium exiting the reactor has an MMA content of more than 20% by weight and less than 50% by weight, has a water content of between 1% and 15% by weight and contains less than 20% by weight of unconverted methacrolein.

8. Process according to at least one of embodiments 1 to 7, characterized in that a combination of at least one classifying sedimentation apparatus and at least 2 filters continuously traversed by the reaction medium containing fines fractions of the catalyst particles are used and the first filter after the at least one classifying sedimentation apparatus has a lower retention capacity than the subsequent second filter.

9. Process according to embodiment 8, characterized in that the classifying sedimentation apparatus(es) are installed within the reactor shell and in that at least one of the downstream filters is arranged outside the reactor shell.

10. Process according to any of embodiments 1 to 9, characterized in that a final filter upstream of the next process operation, preferably upstream of a distillation, a degassing, a phase separation or an extraction, has a retention capacity for particles smaller than 10 µm, with the result that less than 1 ppm of catalyst particles having a diameter greater than 10 µm pass into the next the process operation.

11. Process according to any of embodiments 1 to 10, characterized in that the reaction is performed in a reactor in which the ratio of diameter to height of the gasified liquid level is between 1:1 and 1:50, in that the reactor contains at least two zones A and B and in that present at the transition from zone A to each zone B are internals which homogenize the flow of the reaction mixture upon entry of the reaction mixture into zone B, wherein the ratio of the volume of zone A to the total volume of all zones B is greater than 1 and less than 500.

12. Process according to any of embodiments 1 to 11, characterized in that the reactor comprises one or more feed conduits through which the mixtures of alkyl alcohol and (meth)acrolein may be supplied.

13. Process according to embodiments 8 or 9, characterized in that the classifying sedimentation apparatus, zone C, consists of a plurality of channel-like profiles, tubes or lamellae having an angle of inclination to the horizontal, which each have the same pressure at the inlet.

14. Process according to embodiment 13, characterized in that the sedimentation apparatus is an inclined settler.

15. Process according to at least one of embodiments 8 or 9, characterized in that the sedimentation apparatus is a hydrocyclone.

16. Process according to embodiments 11 to 15, characterized in that the relatively large catalyst particles are retained in the separation apparatus and recycled into zone B, in that the relatively small catalyst particles are collected using at least one filter apparatus and in that zone A in the lower portion of the reactor is actively supplied with an oxygen-containing gas via nozzles or gasification apparatuses and simultaneously at least one zone B comprises no apparatuses for active gasification of the reaction mixture.

17. Process according to embodiments 11 to 16, characterized in that a stirring means or a vertically conveying pump is arranged in zone A and in that zone A and at least one zone B are separated from one another by internals, preferably by dividing walls, wherein the internals at the transition from zone A to each zone B largely prevent entry of gas bubbles into zone B.

18. Process according to embodiments 1 to 17, characterized in that the average catalyst particle size based on the volume distribution is between 50 and 120 µm.

DETAILED DESCRIPTION OF THE INVENTION

In the context of the invention described here, the average particle size distribution is to be understood as meaning the volume-average particle size distribution. This may be determined for example via various sieving steps. In accordance with the invention, a Beckmann Coulter LS particle size measurement was however performed. The basis of the measurement and the measurement principle are elucidated in the standard "*DIN ISO 22412:2019-09 Particle size analysis—Dynamic light scattering (DLS)*". Employed in principle is a diluted suspension which contains in addition to the component to be measured just under 0.1% by weight of sodium pyrophosphate as a stabilizer. The component to be measured is needed in such that an absorbance/scattering of the light source of 10-20% is achieved. The evaluation is based on the principle that all measured objects approximate to spheres. The respective sphere volumes are then plotted as a function of sphere diameter to obtain the particle distribution function. This accordingly results in a volume distribution which may inter alia be converted into a weight distribution using the material density. Volume distribution should always be assumed unless otherwise stated.

The oxidative conversion of (meth)acrolein preferably employs a pulverulent fresh catalyst which comprises gold or palladium as the central active oxidation metal in a concentration of between 0.1% by weight and 10% by weight based on the total weight including further support material. These preferably employed particles of the catalyst have a size of 0.1 to 300 µm, wherein more than 95% by volume of the catalyst particles present have a size of less than 200 µm.

It is also preferable when more than 50% by volume of the catalyst particles have a size between 10 and 90 µm and the fines fraction of the catalyst particles in the reactor having a size of 0.1 µm to 10 µm is less than 10% by volume.

It is particularly preferable when less than 0.5% by weight per hour of the catalyst powder present in the reactor are discharged from the reactor in a classifying manner together with the product solution during the reaction. After 1000 operating hours the catalyst fraction remaining in the reactor comprises catalyst particles which to an extent of at least 98% by volume have a particle size above 10 µm.

The catalyst discharge is in turn collected in at least one further filter which allows retention of particles of 1 to 30 µm and the particles retained in the filters downstream of the inclined settler are to an extent of more than 50% by volume particles smaller than 30 µm.

The employed pulverulent catalyst preferably has an average particle size distribution of 30 to 100 µm based on its volume fractions, wherein these sizes may be reduced through mechanical stress in the case of prolonged, continuous operation. The fines fraction discharged with the reactor medium in turn preferably has an average particle size distribution of 1 to 15 µm which is likewise based on the volume fractions.

It has proven particularly advantageous when a particle collective consisting to an extent of at least 50% by volume of particles smaller than 30 µm is continuously discharged from the reactor. It is moreover advantageous to supply these particles to the filters in suspended form in a reaction medium containing MMA, methacrylic acid, water and methanol.

In preferred embodiments of the present invention, the reaction medium exiting the reactor has an MMA content of more than 20% by weight and less than 50% by weight. In these embodiments the water content is then between 1% and 15% by weight. Less than 20% by weight of unconverted methacrolein is then also present.

It has proven particularly advantageous in the process according to the invention to use a combination of at least one classifying sedimentation apparatus and at least 2 filters. These are continuously traversed by the reaction medium containing fines fractions of the catalyst particles. It is preferable when in addition the first filter after the at least one classifying sedimentation apparatus has a lower retention capacity than the subsequent second filter.

It is particularly preferable when the classifying sedimentation apparatus is installed in the reactor shell in such a way that at least one of the downstream filters is arranged outside the reactor shell.

Additionally or independently of the other embodiments of the present invention it is advantageous when a final filter upstream of the next process engineering operation, preferably upstream of a distillation, a degassing, a phase separation or an extraction, has a retention capacity for particles smaller than 10 µm. This results in less than 1 ppm of catalyst particles having a diameter greater than 10 µm passing into the next the process engineering operation. It is advantageous when this filter is suitable for the separation of particles having a size of at least 1 µm.

The reaction may for example and preferably be performed in a reactor in which the ratio of diameter to height of the gasified liquid level is between 1:1 and 1:50. The reactor comprises here at least three zones A, B and C, wherein present at the transition from zone A to each zone B are internals which homogenize the flow of the reaction mixture upon entry of the reaction mixture into zone B. Each zone B is connected to at least one zone C which comprises a sedimentation apparatus. It is particularly preferable when the ratio of the volume of zone A to the total volume of all zones B in such a reactor is greater than 1 and less than 500. Zone A comprises the reactor.

The reactor preferably comprises one or more feed conduits through which the mixtures of alkyl alcohol and (meth)acrolein may be supplied. The reactor additionally comprises at least one classifying sedimentation apparatus.

It is further preferable when the classifying sedimentation apparatus consists of a plurality of channel-like profiles, tubes or lamellae having an angle of inclination to the horizontal, which each have the same pressure at the inlet and where the liquid flowing therethrough has the same flow velocity at each inlet.

The sedimentation apparatus in zone C is particularly preferably an inclined settler or a hydrocyclone.

Also particularly preferred is an embodiment of the invention in which the relatively large catalyst particles are retained in the sedimentation apparatus and recycled into zone B. It is preferable when the relatively large catalyst particles return to zone A via zone B. In such an embodiment the relatively small catalyst particles which pass through zone C are collected using at least one filter apparatus and simultaneously zone A in the lower portion of the reactor is actively supplied with the oxygen-containing gas via nozzles or gasification apparatuses. Simultaneously, one or more zones B, particularly preferably all zones B, comprise no apparatuses for active gasification of the reaction mixture, thus minimizing gas entry into zone C.

The reaction mixture in zone A may optionally be vertically conveyed with a stirring means or a pump in such a way that the gas bubbles are as small as possible and the gas residence time in zone A is high.

Optionally, in zone A the stirring means is arranged such that zone A and at least one zone B are separated from one another by internals, preferably by dividing walls, wherein the internals at the transition from zone A to each zone B largely prevent entry of gas bubbles into zone B.

The process according to the invention may be performed particularly efficiently when the average catalyst particle size is between 50 and 120 μm.

EXPERIMENTAL SECTION

Methacrolein was produced according to U.S. Pat. No. 4,496,770. However, alternative procedures may also be used, for example that in U.S. Pat. No. 9,580,374.

Example 1 Production of a Pulverulent, Abrasion-Resistant $SiO_2$—$Al_2O_3$—MgO Support Material An enamel-lined receiver was initially charged with 21.36 kg of $Mg(NO_3)_2 \cdot 6H_2O$ and 31.21 kg of $Al(NO_3)_3 \cdot 9H_2O$ and the mixture was dissolved in 41.85 kg of demineralized water while stirring with an impeller stirrer. 1.57 kg of 60% $HNO_3$ was then added while stirring.

166.67 kg of silica sol (Köstrosol 1530AS from Bad Köstritz, 30% by weight $SiO_2$, average particle size: 15 nm) was initially charged in an enamel-lined 500 L reactor and cooled to 15° C. while stirring with an impeller stirrer. 2.57 kg of 60% $HNO_3$ was slowly added to the solution while stirring. At 15° C. the nitrate solution from the receiver was added to the sol over 45 min while stirring. After the addition, the mixture was heated to 50° C. over 30 min and held at this temperature for a further 4 h, the mixture undergoing gelation.

At the end of this time, the gelled mixture was continuously pumped into a spray dryer as a suspension and spray dried at an outlet temperature of 130° C. The dried green product (the mixture initially obtained after spray drying) was calcined in a rotary kiln, wherein the residence time in the hot zone (600° C.) was about 45 minutes. The residence time and throughput time for the calcination in the rotary kiln was controlled via the inclination of the rotary kiln (about 1° to 2° inclination). The nitrous gases occurring during the calcination operation were removed in gaseous form and appropriately treated by absorption and chemisorption.

The passage through the rotary kiln was repeated at identical residence times and identical temperature settings in the hot zone. The nitrate content in the finished support particles was less than 1000 ppm.

After calcination, 55 kg of a white, flowable pulverulent support material were obtained. The mass yield was about 95%.

The support was analysed by SEM and laser diffraction which revealed a spherical support having an average particle size distribution of about 60 μm.

The support was subsequently subjected to classification by sieving with several passes and various sieve sizes, wherein the fractions above 120 μm and below 15 μm were very largely removed. Because of technical limitations, a fines fraction of about 3.6% by volume remained, i.e. particles which despite sieving had a particle size of between 1 and 15 microns. The yield of the classification step (sifting/sieving) was about 70% and the obtained average particle size distribution of the finished support material was about 68 μm.

Example 2 Production of a Nanoparticulate Gold-Containing Catalyst for Continuous Performance of a Direct Oxidative Esterification of Methacrolein to MMA In an enamel-lined reactor, 15 kg of the support was suspended in 50 kg of demineralized water while stirring with an impeller stirrer. The resulting mixture was heated to 90° C. and aged for 15 minutes after reaching 90° C. A solution of 852.9 g of $Co(NO_3)_2 \cdot 6H_2O$ in 7.5 kg of demineralized was metered in over 10 minutes and the mixture was aged for 30 minutes. 3.7 L of 1 molar NaOH solution was then added over 10 minutes. Immediately thereafter, a solution of 376.8 g of auric acid (41% gold) in 7.5 kg of demineralized water was added and the mixture was aged for 30 minutes. The resulting suspension was cooled to 40° C. and filtered using a centrifuge. The filter cake was washed in the centrifuge with demineralized water until the filtrate became clear and had a conductivity below 100 μS/cm.

The wet catalyst was dried at 105° C. in a vacuum drying oven until the residual moisture was below 5%. The dried catalyst was calcined in a rotary kiln, wherein the residence time in the hot zone (450° C.) was about 45 minutes. The yield was about 99%.

The calcined catalyst was analysed by SEM-(EDX) and laser diffraction, which revealed a spherical eggshell catalyst having an average particle size distribution of about 68 μm. The fines fraction was about 5.2% by volume. ICP revealed a gold content of 0.85% by weight.

The catalyst was employed in this form in the continuous oxidative esterification of methacrolein to MMA in example 3.

Example 3 Continuous Performance of a Direct Oxidative Esterification of Methacrolein to MMA I. Reactor, Reaction System and Configuration of the Catalyst Retention System A stirred-tank reactor fitted with a stirrer was used for the reaction. The employed materials are made of conventional stainless steel to withstand the slightly corrosive media. The reactor has a double jacket which is connected to a thermostat which can in turn effect cooling and heating via its medium. The reactor lid is connected to a condenser via a vapor tube (100 mm nominal width).

The stirred tank had an inner diameter of 400 mm and the reactor height up to the lid was 1500 mm. The stirrer is connected to the reactor from below via the base and is fitted with special stirring means which allow both optimal gas dispersion for the oxygen-containing gas (in this case compressed air) and optimal suspension of the particulate catalyst in the medium. A commercial stirrer system consisting of a primary disperser for large gas volumes (Ekato Phasejet) for gas-liquid mixtures having a radial conveying direction and a Kombijet stirring means, i.e. two stirring means secured to the stirrer shaft, is employed. The distance of the stirring means from the base of the reactor was 100 mm and 400 mm for the second stirring means. The gas conduit for supplying the oxygen-containing gas terminates directly below the dispersion means and ensures uniform distribution of the gas over the reactor cross section and fine dispersion of the oxidation gas.

Above the reactor, lid feed conduits for reactants, recycle streams and auxiliaries are instated in the reactor in such a way that the feed conduits terminate wet below the media fill level. The top of the reactor is connected via a conduit with a receiver vessel containing a methanolic stabilizer solution (1000 ppm Tempol).

II. Catalyst Retention System

In the upper portion of the reactor is a take-off tube which passes the reaction suspension into the externally instated inclined settler. The slurry is initially degassed in the degassing vessel (internal diameter 200 mm with conical lower outflow) so that only dissolved gas constituents remain in the slurry suspension. The lower portion of the degassing vessel is connected to a pipeline having a 30 mm internal diameter and constitutes the upper portion of the downcomer. The now degassed, only biphasic suspension thus flows vertically downward to a Y-shaped branching. The right-hand arm of the branching passes the suspension to the inclined settler element where the biphasic system undergoes efficient sedimentation. The catalyst thus returns to the reactor. At the outlet of the inclined settler is a pressure-resistant sightglass to allow visual examination of the quality of the separation as well as a pressure maintenance means and a valve to control the amount removed. Installed downstream of the pressure valve are two parallel filters made of polypropylene which allow a maximum separation performance of 1 micron (according to manufacturer specifications). The filters are continuously traversed and also integrated via a three way valve such that it is possible for only one filter to be traversed while the other may be changed during ongoing operation.

The lamella elements of the inclined settler are cuboidal four-edged profiles made of stainless steel having internal dimensions of: L=700 mm, H=20 mm, W=50 mm. The usable internal volume is thus 700 mL. A total of 8 lamella elements are installed.

III. Commencement of Reaction and Continuous Reaction:

The reactor was charged with a mixture of methanol, water and MMA as well as dissolved Na methacrylate. Initial charging of this reaction mixture results in faster attainment of steady-state concentrations. The reactor was charged with 130 kg of this starting medium having a composition of 3% by weight of methacrylic acid, wherein 50% thereof was in the form of the sodium salt, 33% by weight of MMA, 5% by weight of water and 59% by weight of methanol. The fill level was about 80% of the fill height of the reactor. The reactor is additionally charged with 13 kg of the catalyst according to example 2. The slurry density is thus 10% by weight based on the employed catalyst amount and operating volume of the reaction solution. The reaction mixture is heated to 80° C. and the stirrer set to 260 rpm. The reactor is brought to an operating pressure of 5 bar absolute (using nitrogen as the starting medium). After reaching the reaction temperature, air is introduced in steps of 1 kg/h, thus causing immediate onset of the reaction, as apparent from the fall in the methacrolein level in the reactor and the increase in the MMA concentration in the reaction mixture.

The amount of air is increased in the abovementioned steps until the offgas has an oxygen concentration of 5% by volume. This is advisable, since the explosive limit of the offgas from the reaction is an oxygen content of barely 8% by volume. The temperature of the offgas after condensation of the condensable organic constituents, in particular methanol, methacrolein, MMA, water and low-boilers, is −20° C. NIR is used to measure and quantify the concentration of the various offgas constituents, in particular $CO_2$, CO, oxygen, water, propene, nitrogen, methanol, acetone, methyl formate and optionally other low boilers discharged with the offgas. The offgas having a total content of volatile organic constituents of less than 1.5% by volume is subjected to thermal treatment and incinerated.

Methacrolein is continuously supplied to the reactor via a metering pump. 140 mol of methacrolein is metered into the reactor per hour to establish a steady-state conversion of between 70% and 72%. Over the total running time in continuous operation, a conversion of 98 to 102 mol of methacrolein is determined. According to this operating mode, the reactor is operated with essentially two methacrolein feed streams, namely the fresh methacrolein feed (at a metered addition rate of about 100 mol/h) and the methacrolein recycle feed, this being the top fraction from the MAL-MeOH recycle column. This stream contains about a further 40 mol/h of methacrolein.

The discharge of the steady-state reaction mixture via the catalyst retention system (inclined settler and filtration units) is controlled via a pressure valve and is on average 32.5 kg/h. This corresponds to an average reaction time of about 4 h. The ratio of the discharged volume to the volume of the inclined settler element may be calculated as a defined parameter especially for the quality of the solid separation. In the present example this ratio is about 4.06 kg of liquid per lamella element (700 mL) per hour. One parameter which describes the separation efficiency of the inclined settler is the volume flow of the medium based on the cross-sectional area of the inclined settler; if the resulting formal velocity is less than the descent velocity of the particles/the particle collective, separation of the particles will result. In the present example this parameter is about 0.17 m/h or 0.17 $m^3/m^2 \times h$ (density of 800 $kg/m^3$, lamella area 700 mm×50 mm, projected area scaled with the sine function of the angle of inclination of 60°).

The reaction mixture is decompressed and passed into a column via an intermediate vessel having a volume of 10 L. In this so-called methacrolein-methanol recovery column (operating pressure 1 bar absolute), the methacrolein that is not converted in the reaction and excess methanol condense at the top of the column and are recycled into the reactor. In addition, certain concentrations of other low boilers are condensed in the overhead product of the column. These include inter alia MMA, water, acetone, methyl propionate, methyl formate and methyl acrylate and also further traces of other low-boiling components, some of which form azeotropes with one another and with the main components.

The column is operated at a reflux ratio of 1:1. The bottoms temperature of the column is 72° C. to 73° C. The control parameter of the column is inter alia the residual methacrolein content of the bottom product (bottom discharge), which is typically well below 1% by weight. In continuous operation of the unit, methacrolein contents in the bottoms between 0.05% to 0.2% by weight are achieved.

The bottom product contains crude MMA as well as the higher boiling byproducts of the reaction, in particular methyl methoxyisobutyrate ("MMIB") and methacrylic acid ("MAA") which is in turn partly in the form of the sodium salt. A sequence of extraction and multistage distillation affords MMA of commercial quality and purity.

The selectivity of the reaction is determined by gas chromatography (GC) and is on average 94.4% for MMA, 3.0% for methacrylic acid and 1.2% for MMIB, the respective reference value being the amount of the methacrolein used. Including the losses of the reactants (methacrolein) and MMA, the C4 reconciliation in the offgas comes to virtually 100%.

Figure 1:
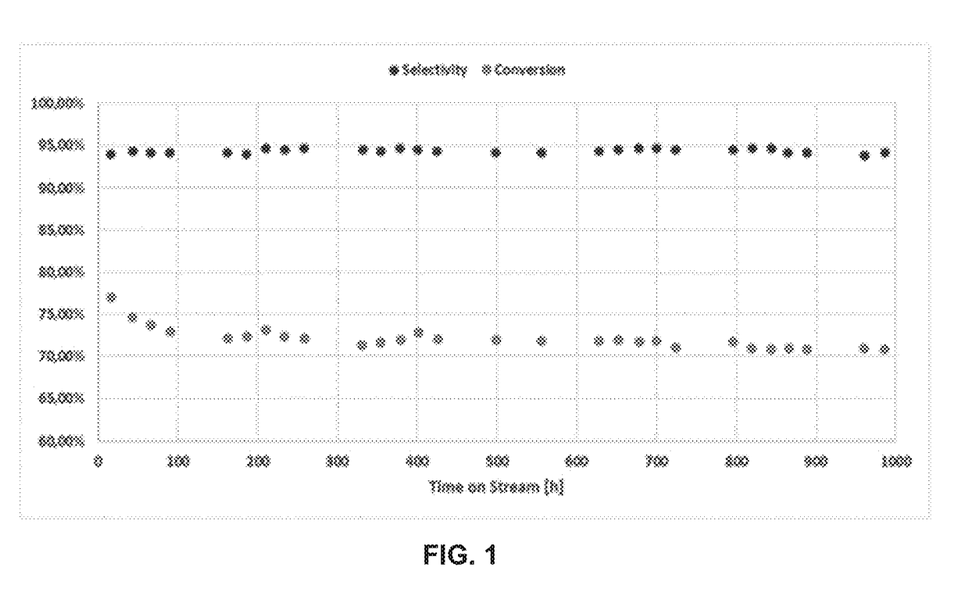
FIG. 1 shows the conversion and selectivity of the reaction according to the invention over a running time of the unit of nearly 1000 operating hours.

The course of the conversion and selectivity over a running time of the unit of nearly 1000 operating hours is shown in FIG. 1.

Figure 2:
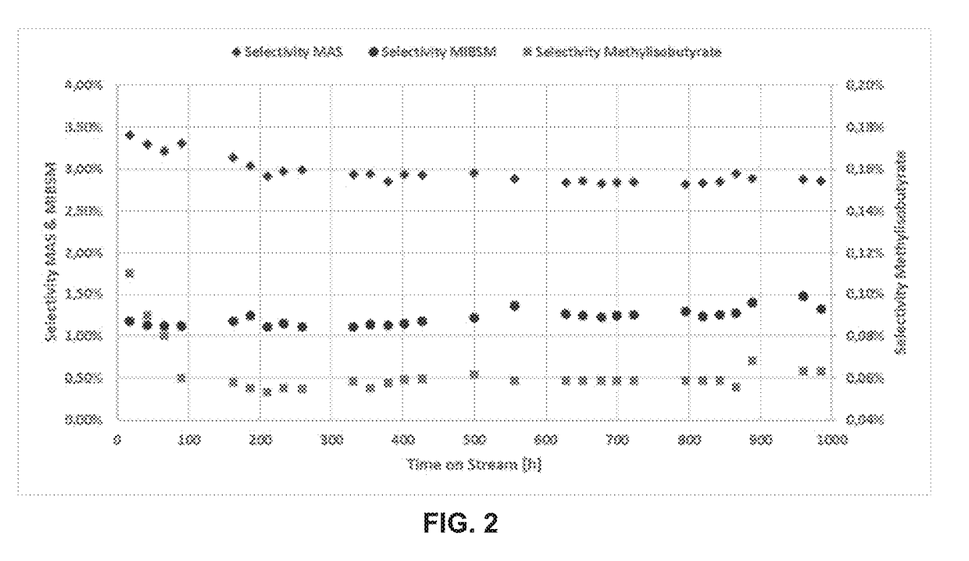
FIG. 2 shows the change of selectively for MAA in the reaction according to the invention.
Figure 3:
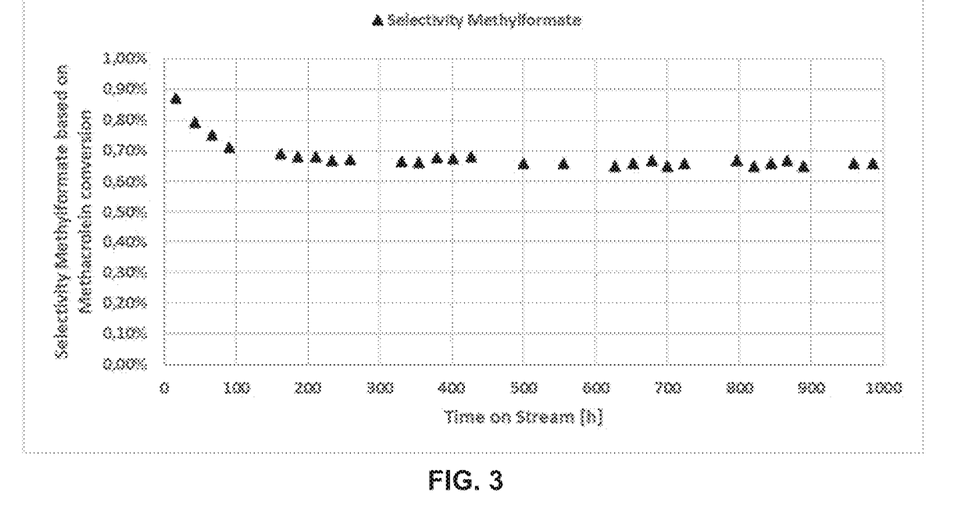
FIG. 3 shows the change in selectively for methyl formate in the reaction according to the invention.

According to the invention the classification in the inclined settler leads to a decrease in catalyst present in the reactor over the first almost 100 hours of operating time, with the result that the conversion of methacrolein falls. The selectivities for MMA and MMIB are unaffected by this, unlike the selectivities for MAA and methyl isobutyrate. The reason for this is firstly the discharging of a—more active—fines fraction which generates more methyl isobutyrate and secondly, for MAA, a deferred change in the water content in the reaction matrix which results in a change in the selectivity for MAA as shown in FIG. 2. A fall in the selectivity for methyl formate surprisingly also results, as shown in FIG. 3. This has several advantages, such as decreased hydrolysis to formic acid, thus causing the NaOH demand of the reaction to fall, and smaller amounts of methyl formate in the offgas stream. Methyl formate can react with water from the offgas at the condensation site to form formic acid and methanol, thus increasing the corrosivity of the offgas condensate.

Figure 4:
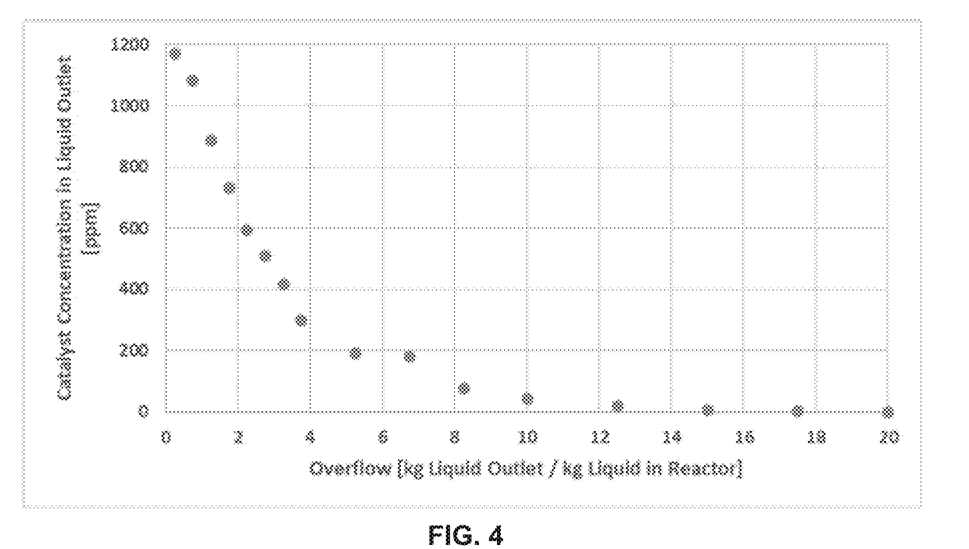
FIG. 4 shows the determination of the catalyst discharge of the invention and catalyst retention as a function of running time.

FIG. 4 shows the determination of the catalyst discharge of the invention and catalyst retention as a function of running time. Time 0 represents fresh catalyst.

The reactor discharge from the above-described continuous reaction was sampled at regular intervals and the amount of catalyst exiting the inclined settler and present therein was determined. To this end, the sample of reaction medium was filtered through a 1 μm depth filter and the residue determined gravimetrically after drying.

Immediately after commencement the suspension still has a concentration of about 1200 ppm of catalyst. This is apparent inter alia from the slight purple coloration of the suspension. The catalyst concentration then rapidly decreases and after barely 20 reactor volumes of discharge, corresponding to a reaction time of 80 to 100 hours, reaches an asymptotic minimum of about 1 ppm. Sampling was then stopped.

Figure 5A:
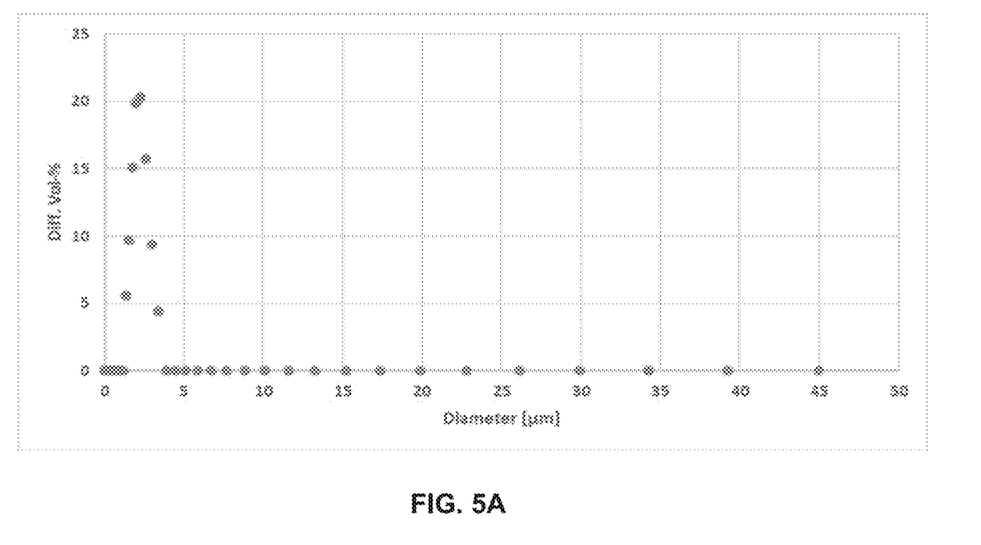
FIG. 5A shows the particle size distribution analysed by the Coulter method of the homogenized catalyst of the final sample.
Figure 5B:
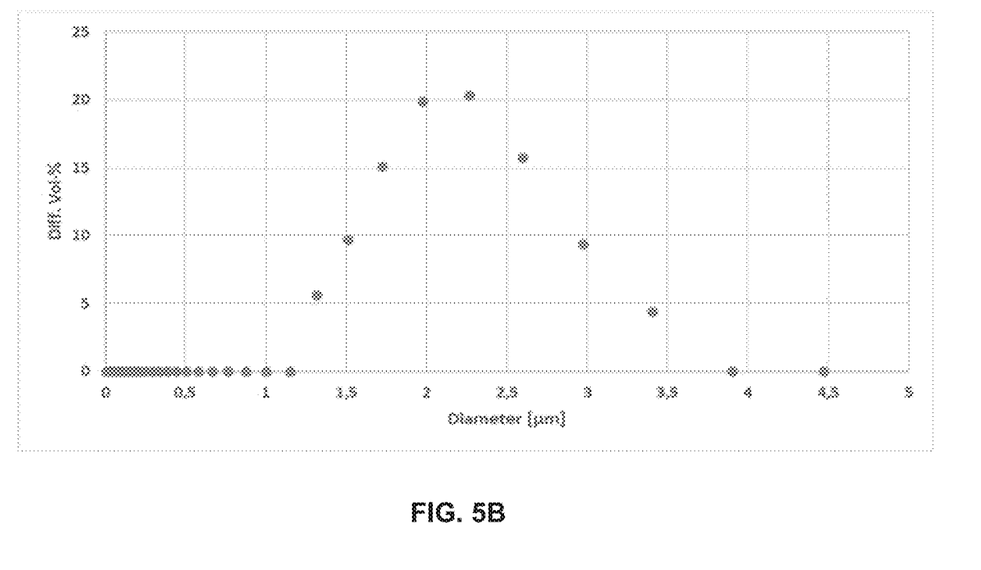
FIG. 5B shows a magnified section of FIG. 5A.

The catalyst of the final sample was homogenized and its particle size distribution analysed by the Coulter method. The result is shown in FIG. 5A. FIG. 5B shows a magnified section.

According to the invention the classifying effect which ensures that only very small residual particles are discharged via the inclined settler is observed. This is consistent with the stable conversion function after almost 100 hours. It was therefore demonstrated that
  a.) over a short operating time of just a few days the disruptive fines fraction of the fresh catalyst is discharged from the reactor effectively and in a classifying manner by the present inventive catalyst retention system, that
  b.) this discharge can be very largely recovered and subsequently recycled with a fine filter, and that
  c.) after this startup and conditioning phase, the conversion and the steady-state reaction concentration remain stable, thus allowing problem-free operation of the workup portion without substantial adaptation of the operating parameters.

Figure 6:
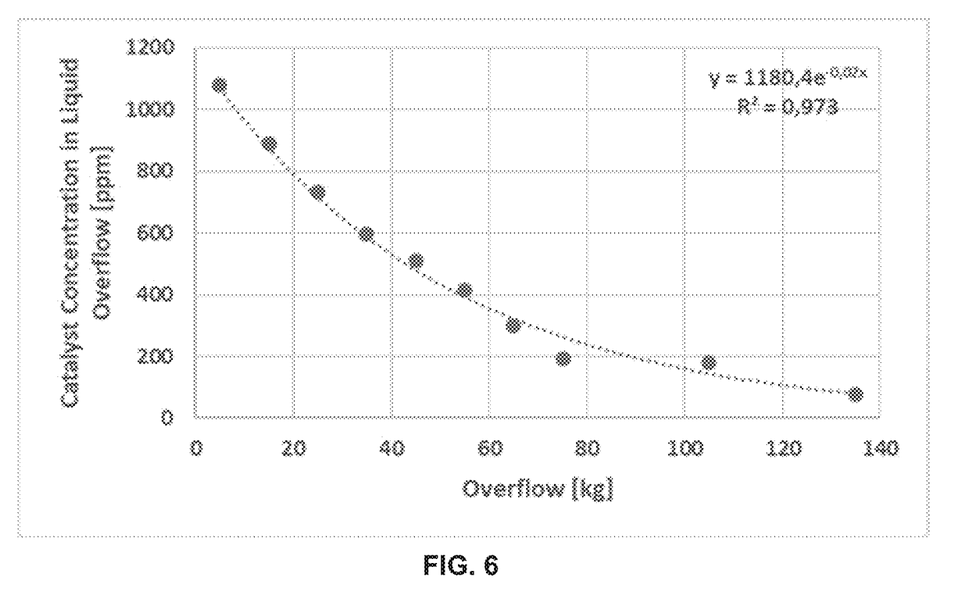
FIG. 6 shows the time-course of the catalyst concentration in the reactor discharge as a function of discharge volume.

FIG. 6 shows the time-course of the catalyst concentration in the reactor discharge as a function of discharge volume.

Example 4 Continuous Performance of a Direct Oxidative Esterification of Methacrolein to MMA The reaction is performed with the same reactor setup as described in example 3. The catalyst from example 2 is employed. The slurry density is in turn 10% by weight based on the steady-state reaction medium. However, the means for primary retention of the catalyst is now installed internally in the reactor.

Arranged in the upper portion of the reactor is an overflow, about 150 mm below the steady-state operation fill level. The slurry thus overflows freely in the upper portion. The slurry is initially degassed in the degassing vessel (internal diameter 200 mm with conical lower outflow) so that only dissolved gas constituents remain in the slurry suspension. The lower portion of the degassing vessel is connected to a pipeline having a 30 mm internal diameter and constitutes the upper portion of the downcomer. The now degassed, only biphasic suspension thus flows vertically downward to a Y-shaped branching. The right-hand arm of the branching passes the suspension to the inclined settler element where the biphasic suspension undergoes efficient sedimentation. At the outlet of the inclined settler is a pressure-resistant sight glass to allow visual examination of the quality of the separation as well as a pressure maintenance means and a valve to control the amount removed. Installed downstream of the pressure valve are two parallel filters made of polypropylene which allow a maximum separation performance of 1 micron (according to manufacturer specifications). The filters are continuously traversed and also integrated via a three way valve such that it is possible for only one filter to be traversed while the other may be changed during ongoing operation.

The lamella elements of the inclined settler are cuboidal four-edged profiles made of stainless steel having internal dimensions of: L=700 mm, H=20 mm, W=50 mm. The usable internal volume is thus 700 mL. A total of 8 lamella elements are installed.

The reactor is brought online as described in example 3 and initially operated without feed streams for one hour until a steady-state circulation is ensured in the reactor and in the downcomer. Removal of 65 kg/h is then established and the feed streams are supplied. Half of the discharge is recycled to the reactor after cooling to 40° C. and supply of the stream is thus effected in the lower third of the reactor. Similarly to example 3, the following parameters are established: 8.1 kg of liquid per lamella element per hour; the loading of the settler is thus 0.34 m/h or 0.34 m$^3$/h m$^2$. This relatively high rate means that a relatively high discharge of catalyst is to be expected.

100 mol of fresh methacrolein is metered in per hour, as well as a further 40 mol of methacrolein from the recycle stream from the column. The air consumption over the entire operating time is about 8500 L. A residual oxygen concentration of 4% to 4.5% by volume is established in the offgas. Under these conditions the space-time yield of the catalyst is about 7.5 to 8 mol of MMA/h/kg of catalyst.

The unit is operated continuously for 7 days. During this time one filter is continuously traversed and the starting back pressure of the 1 micron PP filter is about 100 mbar. There is a continuous buildup of pressure during this first operating time through loading of the filter; after an operating time of 7 days this pressure is about 900 mbar.

After this first operation time of 168 h, a switchover from the first filter to the second filter is effected.

The unit is continuously operated for a further 10 days and the crude product is continuously discharged via the second filter. In this second operating phase, the pressure increase due to the new filter is markedly lower.

For the reconciliation, the two filters are washed with water, first carefully in a recirculating air stream in an oven at 70° C. and then at 120° C. for a further 12 h. The weight and particle size of the filtered catalyst fines fraction is then determined. These results are reported in table 1 which follows.

After the total operating time of 308 hours, the reaction is stopped by terminating the metered addition of methacrolein. The reactor is gasified at operating temperature for a further 16 hours, resulting in a residual methacrolein content of less than 0.2% by weight. The reactor contents are then discharged through a filter, the catalyst is washed and dried and the dried powder is subjected to treatment at 400° C. in air in a muffle furnace. Finally, the residual mass is determined. 12.75 kg of catalyst are found. This corresponds to about 93% of the catalyst amount initially employed.

TABLE 1

|  | Example 4, first phase | Example 4, second phase |
|---|---|---|
| Experiment duration [h] | 168 | 240 |
| Experiment phase [h] | 0 to 168 | 168 to 308 |
| Crude product discharged [kg] | 5460 | 7800 |
| Catalyst discharge in filter [g] | 158 | 52 |
| MMA produced [kg] | 1911 | 2730 |
| Specific fines discharge [mg/kg MMA] | 82 | 19 |

Conclusion: Converting from the specific discharge rate, 19 g of catalyst per ton of MMA is discharged from the reactor. Assuming that the catalyst has a noble metal content of 1% by weight, this would correspond to 190 mg of gold, which in turn would correspond to a value of about 8 US$/ton of MMA of gold in the fine filter (assuming a hypothetical price of an ounce of gold of 1400 US$/ounce). The loss is correspondingly low, while the reaction makes marked gains in selectivity and the fines fraction of the catalyst causes no problems during product workup. In addition, a major part of the discharged fines fraction may even be subsequently recycled.

Example 4b) Continuous Performance of a Direct Oxidative Esterification of Methacrolein to MMA In the same setup as in example 4, a narrowing was welded to the ends of the respective lamellae. The narrowing had only 1.6% of the opening compared to example 4.

The narrowing of the lamellae had the result that the discharge in both phases was reduced by a factor of about 2-4 depending on whether phase 1 or 2 is considered.

|  | Example 4, first phase | Example 4, second phase |
|---|---|---|
| Experiment duration [h] | 168 | 240 |
| Experiment phase [h] | 0 to 168 | 168 to 308 |
| Crude product discharged [kg] | 5456 | 7792 |
| Catalyst discharge in filter [g] | 48 | 24 |
| MMA produced [kg] | 1909 | 2728 |
| Specific fines discharge [mg/kg MMA] | 25 | 9 |

The invention claimed is:

1. A process for producing alkyl (meth)acrylates, comprising:
   reacting (meth)acrolein with an alkyl alcohol in a reactor, in the presence of an oxygen-containing gas and a particulate, pulverulent catalyst in a liquid phase, to obtain an alkyl (meth)acrylate;
   wherein a reaction medium is discharged from the reactor during the reaction, wherein the reaction medium comprises a first portion of the catalyst and a product solution, wherein the first portion of the catalyst is discharged in a classifying manner,
   wherein a second portion of the catalyst remaining in the reactor has a higher particle size distribution compared to the first portion of the catalyst,
   wherein the first portion of the catalyst is collected in at least one filter,
   wherein, optionally, the first portion of the catalyst is at least partially recycled into the reactor, and
   wherein, optionally, the first portion of the catalyst is at least partially removed and sent to a workup for recovery of at least one employed catalyst metal of the catalyst.

2. The process according to claim 1, wherein the catalyst is a fresh catalyst which comprises gold or palladium as a central active oxidation metal in a concentration of between 0.1% by weight and 10% by weight, based on a total weight of the catalyst, wherein the catalyst includes a further support material,
   wherein particles of the catalyst have a size of 0.1 to 300 µm, wherein more than 95% by volume of the particles present have a size of less than 200 µm, and
   wherein more than 50% by volume of the particles have a size between 10 and 90 µm, and
   wherein a fines fraction of the particles in the reactor having a size of 0.1 µm to 10 µm is less than 10% by volume.

3. The process according to claim 1, wherein less than 0.5% by weight per hour of the catalyst present in the reactor is discharged from the reactor,
   wherein in the second portion of the catalyst remaining in the reactor after 1000 operating hours, more than 98% by volume of all catalyst particles have a particle size greater than 10 µm,
   wherein the first portion of the catalyst is collected in the at least one filter which allows retention of particles of 1 to 30 µm in size, and
   wherein catalyst particles retained in further filters downstream of an inclined settler are to an extent of more than 50% by volume of particles smaller than 30 µm.

4. The process according to claim 1, wherein the catalyst has an average particle size distribution of 30 to 100 µm, and wherein a fines fraction of the first portion of the catalyst discharged in the reaction medium has an average particle size distribution of 1 to 15 µm.

5. The process according to claim 1, wherein the alkyl alcohol is methanol and the alkyl (meth)acrylate is methyl methacrylate (MMA).

6. The process according to claim 5, wherein the first portion of the catalyst comprises at least 50% by volume of particles smaller than 30 μm and is continuously discharged from the reactor, and is supplied to the at least one filter in a suspended form in the reaction medium containing the MMA, methacrylic acid, water, and the methanol.

7. The process according to claim 5, wherein the reaction medium exiting the reactor has an MA content of more than 20% by weight and less than 50% by weight, has a water content of between 1% and 15% by weight, and contains less than 20% by weight of unconverted methacrolein.

8. The process according to claim 1, wherein the reaction medium is discharged to a combination of at least one classifying sedimentation apparatus and at least 2 filters continuously traversed by the reaction medium, and
wherein a first filter of the at least 2 filters after the at least one classifying sedimentation apparatus has a lower retention capacity than a subsequent second filter of the at least 2 filters.

9. The process according to claim 8, wherein the at least one classifying sedimentation apparatus is installed within a reactor shell of the reactor, and wherein at least one downstream filter is arranged outside the reactor shell.

10. The process according to claim 1, wherein a final filter upstream of a next process operation has a retention capacity for particles smaller than 10 μm, with a result that less than 1 ppm of catalyst particles having a diameter greater than 10 μm pass into the next process operation.

11. The process according to claim 1, wherein the reactor has a ratio of diameter to height of a gasified liquid level of between 1:1 and 1:50,
wherein the reactor contains a zone A and at least one zone B, and wherein present at a transition from zone A to each of the at least one zone B are internals which homogenize flow of a reaction mixture upon entry of the reaction mixture into the at least one zone B, wherein a ratio of a volume of zone A to a total volume of all of the at least one zone B is greater than 1 and less than 500.

12. The process according to claim 1, wherein the reactor comprises one or more feed conduits through which mixtures of the alkyl alcohol and the (meth)acrolein may be supplied.

13. The process according to claim 8, wherein the at least one classifying sedimentation apparatus, in a zone C of the reactor, consists of a plurality of channel-like profiles, tubes, of lamellae having an angle of inclination to a horizontal, wherein each have the same pressure at an inlet.

14. The process according to claim 13, wherein the at least one classifying sedimentation apparatus is an inclined settler.

15. The process according to claim 8, wherein the at least one classifying sedimentation apparatus is a hydrocyclone.

16. The process according to claim 11, wherein relatively large catalyst particles are retained in a separation apparatus and are recycled into the at least one zone B,
wherein relatively small catalyst particles are collected using at least one filter apparatus, and
wherein zone A in a lower portion of the reactor is actively supplied with the oxygen-containing gas via nozzles or gasification apparatuses, and simultaneously the at least one zone B comprises no apparatuses for active gasification of the reaction mixture.

17. The process according to claim 11, wherein a stirring means or a vertically conveying pump is arranged in zone A and wherein zone A and the at least one zone B are separated from one another by the internals, wherein the internals at the transition from zone A to each of the at least one zone B largely prevent entry of gas bubbles into the at least one zone B.

18. The process according to claim 1, wherein an average particle size of the catalyst based on volume distribution is between 50 and 120 μm.

19. The process according to claim 10, wherein the next process operation is a distillation, a degassing, a phase separation, or an extraction.

20. The process according to claim 17, wherein the internals are dividing walls.

* * * * *